(12) United States Patent
Pedersen et al.

(10) Patent No.: US 11,464,912 B2
(45) Date of Patent: Oct. 11, 2022

(54) DRUG DELIVERY DEVICE WITH ZERO POSITION ADJUSTMENT FEATURE

(71) Applicant: Novo Nordisk A/S, Bagsvaerd (DK)

(72) Inventors: Bennie Peder Smiszek Pedersen, Haslev (DK); Thomas Rosengaard Poulsen, Slangerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 212 days.

(21) Appl. No.: 16/302,417

(22) PCT Filed: May 29, 2017

(86) PCT No.: PCT/EP2017/062908
§ 371 (c)(1),
(2) Date: Nov. 16, 2018

(87) PCT Pub. No.: WO2017/207496
PCT Pub. Date: Dec. 7, 2017

(65) Prior Publication Data
US 2019/0275259 A1    Sep. 12, 2019

(30) Foreign Application Priority Data

May 30, 2016    (EP) ..................... 16171890

(51) Int. Cl.
*A61M 5/315*    (2006.01)
*A61M 5/20*    (2006.01)
*A61M 5/31*    (2006.01)

(52) U.S. Cl.
CPC .......... *A61M 5/31556* (2013.01); *A61M 5/20* (2013.01); *A61M 5/31541* (2013.01);
(Continued)

(58) Field of Classification Search
CPC ............ A61M 5/31556; A61M 5/3155; A61M 5/31551; A61M 5/31558; A61M 5/31548;
(Continued)

(56) References Cited

U.S. PATENT DOCUMENTS 5,469,294 A    11/1995    Wilt et al.
6,966,897 B2    11/2005    Shimazaki
(Continued)

FOREIGN PATENT DOCUMENTS

CN    104519930 A    4/2015
CN    105102043 A    11/2015
(Continued)

*Primary Examiner* — Niljay J Shah
(74) *Attorney, Agent, or Firm* — Wesley Nicolas

(57) ABSTRACT

A method of manufacturing a pen drug delivery device comprising the steps of (i) providing a drug delivery device comprising a dose indicator member adapted to move relative to a housing during dose setting and dose expelling corresponding to an axis of rotation, the indicator member having an initial position corresponding to no dose amount being set, (ii) arranging the indicator member in the initial rotational position, and (iii) providing on the housing and on the indicator member respectively a pair of zero markers having a predetermined rotational offset. By this arrangement the issue of finding the correct initial (zero) rotational position of the indicator member is addressed by providing corresponding and rotationally paired zero markings on the pen housing and the indicator member after the pen device has been assembled, this allowing the "true" initial position to be detected by image capture and subsequent image analysis.

33 Claims, 9 Drawing Sheets

(52) U.S. Cl.
CPC ....... *A61M 5/31568* (2013.01); *A61M 5/3155* (2013.01); *A61M 5/31553* (2013.01); *A61M 5/31583* (2013.01); *A61M 2005/3126* (2013.01); *A61M 2207/00* (2013.01)

(58) Field of Classification Search
CPC ................ A61M 5/20; A61M 5/31541; A61M 5/31568; A61M 5/31553; A61M 5/31583
See application file for complete search history.

(56) References Cited

U.S. PATENT DOCUMENTS

| | | | |
|---|---|---|---|
| D652,136 S * | 1/2012 | Hawley | D24/113 |
| 8,556,866 B2 | 10/2013 | Krulevitch et al. | |
| 8,864,021 B1 | 10/2014 | Vitello | |
| 10,179,207 B2 | 1/2019 | Haupt | |
| 10,668,223 B2 | 6/2020 | Bayer et al. | |
| 10,967,133 B2 | 4/2021 | Pedersen et al. | |
| 2005/0033244 A1 | 2/2005 | Veasey et al. | |
| 2007/0244436 A1* | 10/2007 | Saiki | A61M 5/31551 604/131 |
| 2009/0318865 A1 | 12/2009 | Moller et al. | |
| 2010/0249693 A1 | 9/2010 | Links | |
| 2010/0324495 A1* | 12/2010 | Jones | A61M 5/31585 604/207 |
| 2010/0324528 A1* | 12/2010 | Plumptre | A61M 5/31563 604/506 |
| 2013/0197447 A1 | 8/2013 | Smith | |
| 2013/0245543 A1 | 9/2013 | Gerg et al. | |
| 2013/0245566 A1* | 9/2013 | De Sausmarez Lintell | A61M 5/3156 604/246 |
| 2014/0114277 A1 | 4/2014 | Eggert et al. | |
| 2014/0188075 A1 | 7/2014 | Eggert et al. | |
| 2015/0290396 A1 | 10/2015 | Nagar et al. | |
| 2016/0051765 A1 | 2/2016 | Morris et al. | |
| 2019/0192782 A1 | 6/2019 | Pedersen et al. | |
| 2019/0262541 A1 | 8/2019 | Christensen | |

FOREIGN PATENT DOCUMENTS

| | | |
|---|---|---|
| CN | 105530970 A | 4/2016 |
| WO | 2010/037828 A1 | 4/2010 |
| WO | 2010052275 A2 | 5/2010 |
| WO | 2010128493 A2 | 11/2010 |
| WO | 2011117212 A1 | 9/2011 |
| WO | 2013004843 A1 | 1/2013 |
| WO | 2013120776 A1 | 8/2013 |
| WO | 2014111336 A1 | 7/2014 |
| WO | 2014161952 A1 | 10/2014 |
| WO | 2014173434 A1 | 10/2014 |
| WO | 2014173768 A1 | 10/2014 |
| WO | 2014173773 A1 | 10/2014 |
| WO | 2015071354 A1 | 5/2015 |
| WO | 2015082303 A1 | 6/2015 |
| WO | 2015110520 A1 | 7/2015 |
| WO | 2015/136513 A1 | 9/2015 |
| WO | 2015138093 A2 | 9/2015 |
| WO | 2015181192 A1 | 12/2015 |
| WO | 2016001300 A1 | 1/2016 |
| WO | 2016/030348 A1 | 3/2016 |
| WO | 2017148857 | 9/2017 |
| WO | 2017207495 A1 | 12/2017 |

* cited by examiner

DRUG DELIVERY DEVICE WITH ZERO POSITION ADJUSTMENT FEATURE

CROSS-REFERENCE TO RELATED APPLICATIONS

This application is a 35 U.S.C. § 371 National Stage application of International Application PCT/EP2017/062908 (published as WO 2017/207496), filed May 29, 2017, which claims priority to European Patent Application 16171890.3, filed May 30, 2016, the contents of all above-named applications are incorporated herein by reference.

The present invention generally relates to medical devices for which the generation, collecting and storing of data are relevant. In specific embodiments the invention relates to devices, methods and systems for capturing drug delivery dose data in a reliable and efficient way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug delivery devices have greatly improved the lives of patients who must self-administer drugs and biological agents. Drug delivery devices may take many forms, including simple disposable devices that are little more than an ampoule with an expelling means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical per-sonnet's decision making with respect to future medication. Accordingly, it may be desirable to automate the logging of injection information from medication delivery systems. Indeed, what can be detected and logged automatically will in most cases be the amount of drug expelled from the device which then has to be assumed to represent the injected amount of drug.

Though some drug delivery devices integrate this monitoring/acquisition mechanism into the device itself, e.g. as disclosed in US 2009/0318865 and WO 2010/052275, most devices of today are without it. The most widely used drug delivery devices are purely mechanical devices being either durable or prefilled. The latter devices come with a sealed drug container which cannot be removed or replaced without destroying the device which are thus to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2013/120776 describes an electronic supplementary device (or "add-on module") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialled into the drug delivery device. A further external device for a pen device is shown in WO 2014/161952. As any given drug delivery device is manufactured with tolerances for each component also scale drum dose size indication accuracy will potentially vary for each device, e.g. for any given set dose the corresponding scale drum indicia, e.g. a line marking, may not be perfectly aligned with a housing pointer structure, this potentially resulting in inaccuracies when determining scale drum position and thus an incorrect determination of an expelled dose size. WO 2015/082303 and WO 2015071354 disclose examples of such devices in which scale drum position typically will vary due to tolerances in the manufacturing process.

Having regard to the above, it is an object of the present invention to provide devices and methods allowing reliable and cost-effective operation and manufacturing of a drug delivery assembly comprising a user-mountable logging module.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a method of manufacturing a drug delivery device is provided, the method comprising the steps of (i) providing a drug delivery device comprising a housing and a moveable indicator member having an initial position relative to the housing, (ii) arranging the indicator member in an initial position, and (iii) providing on the housing and on the indicator member respectively a pair of zero markers having a predetermined offset.

By this arrangement the issue of finding the correct initial (zero) position of the indicator member is addressed by providing corresponding and paired zero markings on the pen housing and the indicator member after the pen device has been assembled, this allowing the "true" initial position to be detected by image capture and subsequent image analysis. The defined initial position relative to the housing may be an initial rotational position relative to the housing.

When in step (ii) it is defined that the indicator member is being arranged in an initial position, e.g. initial rotational position, this also covers situations in which the indicator member has been arranged in its initial position during manufacturing, the step comprising ensuring that this is the case.

The provided drug delivery device may comprise a drug reservoir or a compartment for receiving a drug reservoir, drug expelling means comprising a dose setting member allowing a user to set a dose amount of drug to be expelled, the indicator member adapted to rotate relative to the housing during dose setting and dose expelling corresponding to an axis of rotation, the amount of rotation corresponding to a set dose respectively the amount of drug remaining to be expelled from a reservoir by the expelling means, the indicator member having an initial rotational position corresponding to no dose amount being set, a housing comprising a window allowing a user to observe a portion of the indicator member, the window being surrounded by an edge portion formed by the housing, and a pattern arranged circumferentially or helically on the indicator member and comprising a plurality of indicia, the currently observable indicia indicating to a user the size of a currently set dose amount of drug to be expelled, the indicator member thereby forming a scale drum.

The pair of zero markers may comprise a housing zero marker and an indicator member zero marker, wherein at least one of the first and second zero markers is provided in step (iii), i.e. the defined pair of zero markings is provided by the addition of a further zero marking to an existing zero marker or by providing a pair of zero markings. More specifically, the housing zero marker may be provided on the housing prior to step (iii) with the indicator member zero marker being provided on the indicator member in step (iii), or the indicator member zero marker may be provided on the indicator member prior to step (iii), with the housing zero marker being provided on the housing in step (iii), or both the housing zero marker and the indicator member zero marker may be provided on the housing respectively the indicator member in step (iii).

The zero markers can be provided by any suitable technology, e.g. by means of laser printing, contact printing, inkjet printing, embossing or engraving. Two zero markers may be provided using the same or two different technologies. A zero marking provided prior to step (iii) may be formed integrally with the given component of the drug delivery device during moulding of that component.

In an exemplary embodiment the rotational offset is zero, just as the pair of zero markers may be arranged in the vicinity of each other. The window may be in the form of an opening which may be provided with a chamfered edge portion is chamfered. The housing zero marker may be provided on the chamfer. Alternatively, the window comprises a transparent member arranged in an opening in the housing. The transparent member may be pre-mounted or it may be mounted in the opening after step (iii). In case the transparent member is pre-mounted an indicator member zero marker may be provided through the transparent member by e.g. laser printing with the laser energy being transmitted through the transparent member and absorbed on the surface of the indicator member.

The drug delivery devices may be prefilled provided with a sealed drug container which cannot be removed or replaced without destroying the device which are thus to be discarded after being emptied.

In a further aspect of the invention a method of manufacturing a drug delivery system is provided, the system comprising first and second drug delivery devices each manufactured as described above, the first drug delivery device being prefilled comprising a drug reservoir with a first type of drug formulation, a zero marker comprising a code indicative of the first type of drug formulation, and the second drug delivery device being prefilled comprising a drug reservoir with a second type of drug formulation, a zero marker comprising a code being indicative of the second type of drug formulation. The code may be a visual code provided on the drug delivery devices after they have been manufactured.

Thus, in an aspect of the invention a method of manufacturing a drug delivery device is provided, the method comprising the steps of (i) providing a drug delivery device main portion comprising a dose setting and expelling mechanism, (ii) attaching to the main portion a drug cartridge comprising a given drug formulation, and (iii) providing on the main portion a marker indicative of the given drug formulation, e.g. a visual code marking which may or may not be visible to the human eye.

The dose setting and expelling mechanism may comprise a rotatable indicator member having an initial rotational position, wherein the indicator member is arranged in the initial rotational position prior to the marker being provided on the indicator member. The code marking may provide at least a portion of the above-described zero marker. The cartridge may be attached using a cartridge holder adapted to be mounted on the device main portion.

As used herein, the term "insulin" is meant to encompass any drug-containing flowable medi-cine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

Figure 1A:
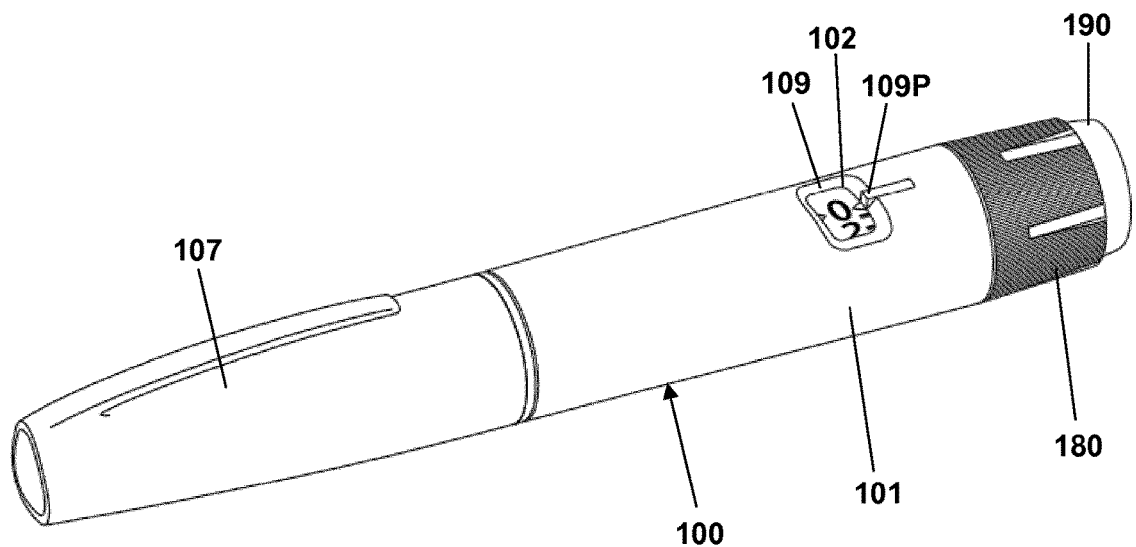
FIG. 1A shows a pen device.

When in the following terms such as "upper" and "lower", "right" and "left", "horizontal" and "vertical" or similar relative expressions are used, these only refer to the appended figures and not necessarily to an actual situation of use. The shown figures are schematic represen-tations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a prefilled drug delivery will be described, such a device providing the basis for the exemplary embodiments of the present invention. Although the pen-formed drug delivery device 100 shown in FIGS. 1-3 may represent a "generic" drug delivery device, the actually shown device is a FlexTouch® prefilled drug delivery pen as manufactured and sold by Novo Nordisk A/S, Bagsvrd, Den-mark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the push/release button 190 is actuated. The window is surrounded by a chamfered edge portion 109 and a dose pointer 109P. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
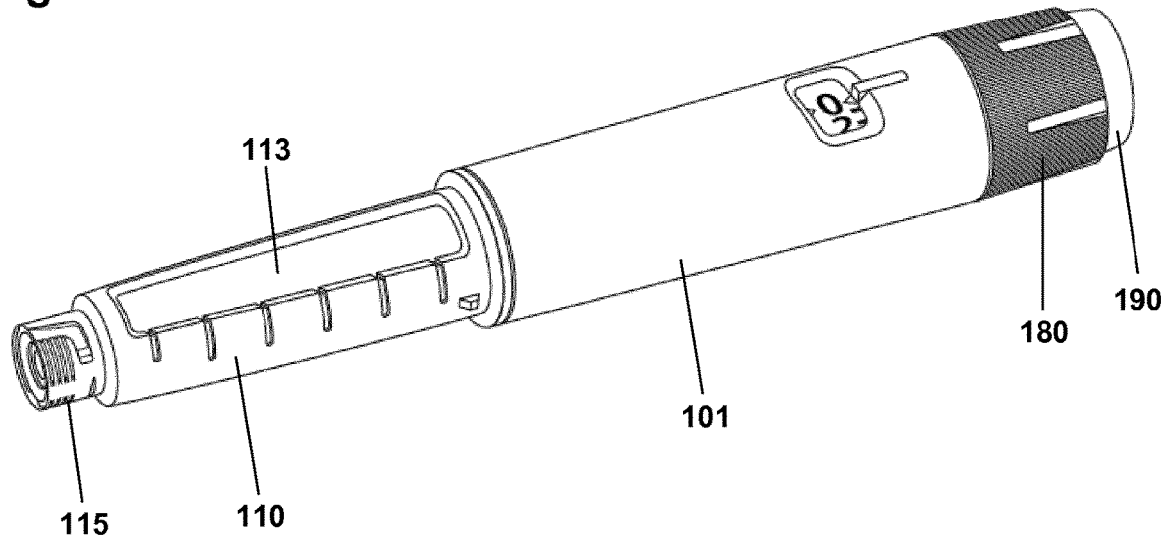
FIG. 1B shows the pen device of FIG. 1A with the pen cap removed.

Although FIG. 1 shows a drug delivery device of the prefilled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to a drug delivery device adapted to interact with an electronically controlled add-on logging device, an exemplary embodiment of such a drug delivery device will be described for better understanding of the invention.

Figure 2:
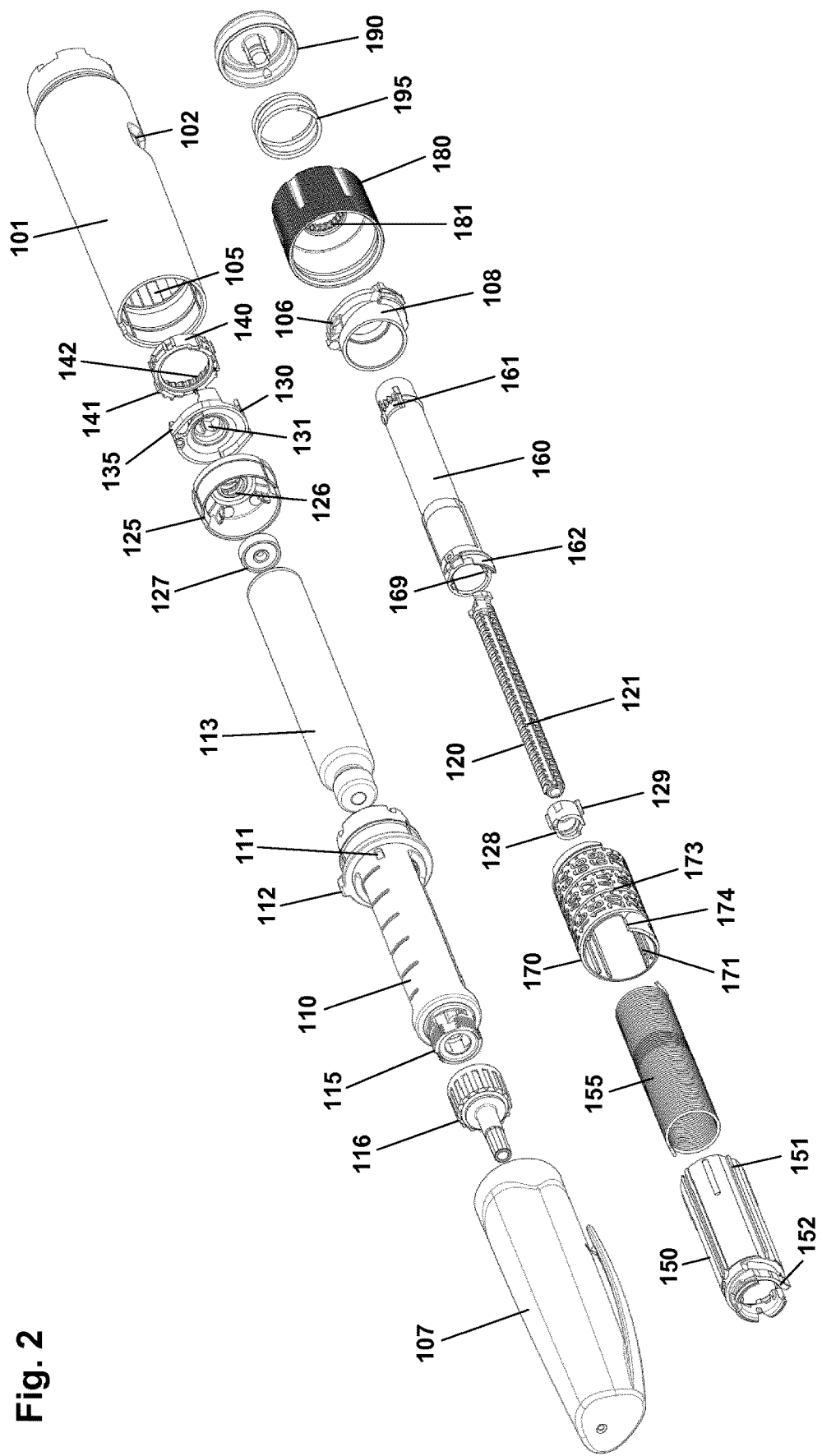
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasable mounted, proximal coupling means in the form of two opposed protrusions 111 allowing a cap 107 to be releasable mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves 121 and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 3B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

The dial system comprises a ratchet tube 150, a reset tube 160, a scale drum 170 with an outer helically arranged pattern forming a row of dose indicia, a user-operated dial member 180 for setting a dose of drug to be expelled, a push/release button 190 and a torque spring 155 (see FIG. 3). The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
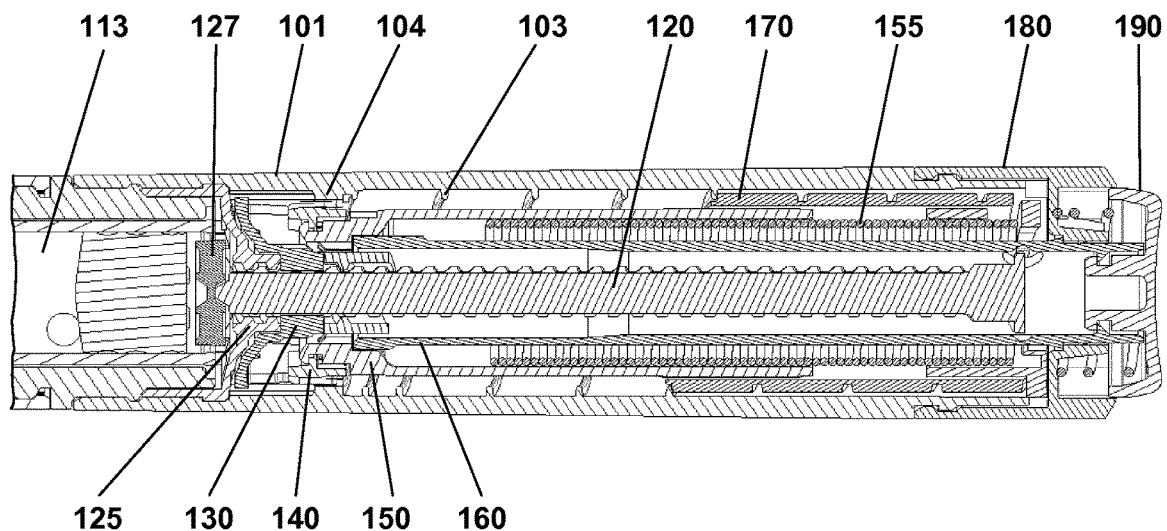

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it. As the ratchet tube is connected to the distal end of the torque spring 155, the spring is loaded. During dose setting, the ratchet arm 152 of the ratchet performs a dial click for each unit dialled due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet arm 152, inner teeth structure 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
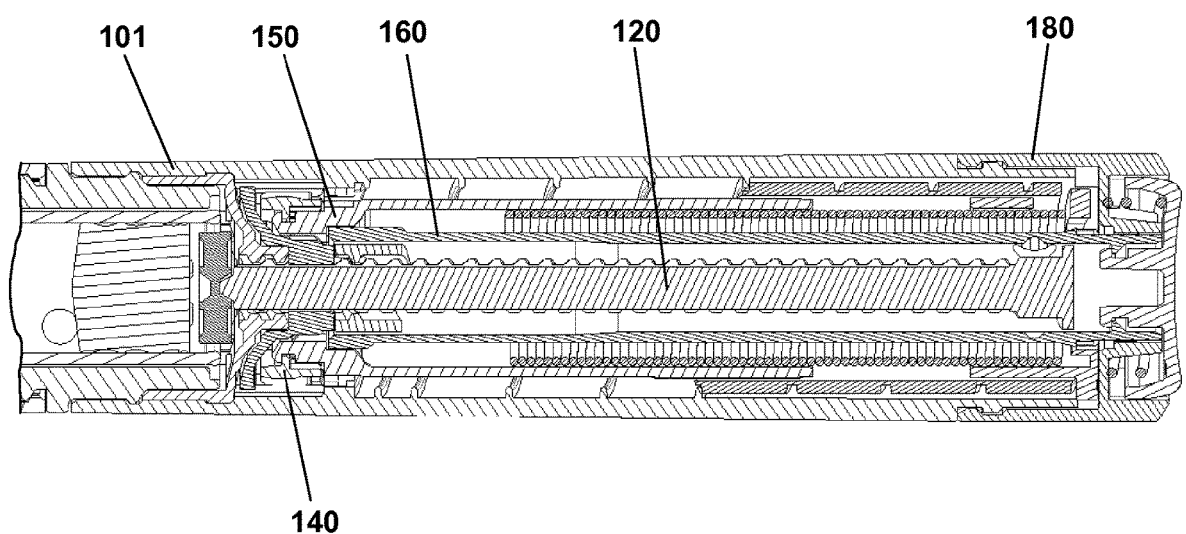

To deliver a set dose, the push/release button 190 is pushed in the distal direction by the user as shown in FIG. 3B. The reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A set dose of less than 5 IU normally cannot be paused, since the rubber piston is compressed very quickly leading to a compression of the rubber piston and subsequently delivery of insulin when the piston returns to the original dimensions. This said, a larger dose can be paused with only a few IU left to be expelled, e.g. as little as 1 IU.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexi-bility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 181 engaging a number of corresponding teeth arranged on a flexible carrier portion 161 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, embodiments of an add-on logging device will be described.

Figure 4:
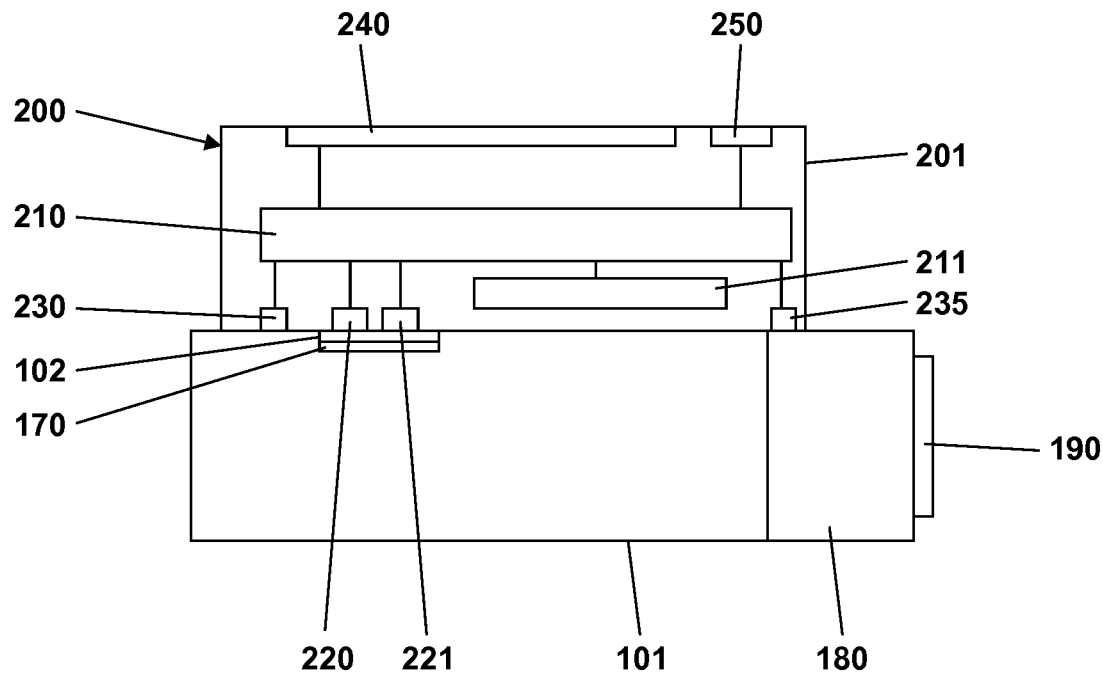
FIG. 4 shows a schematic representation of an add-on device.

FIG. 4 shows a schematic representation of an add-on device 200 in a state where it has been mounted on the housing 101 of a drug delivery device 100 of the above-described pen type. The add-on device is adapted to determine the amount of drug expelled from the drug delivery device during an expelling event, i.e. the subcutaneous injection of a dose of drug. In the shown embodiment determination of an expelled dose of drug is based on determination of scale drum position at the beginning and at the end of the expelling event. To determine the rotational position of the scale drum the dose numerals as seen in the display window 102 may be captured and used. Actual determination of scale drum position may be performed using e.g. template matching (see below) or optical character recognition (OCR). Alternatively a dedicated code pattern may be provided on the scale drum as disclosed in e.g. WO 2013/004843.

The add-on device comprises a housing 201 in which is arranged electronic circuitry 210 powered by an energy source 211. The electronic circuitry is connected to and interacts with a light source 220 adapted to illuminate at least a portion of the scale drum indicator member 170 seen in the window 102, an image capture device (camera) 221 adapted to capture image data from the scale drum, a mounting switch 230 adapted to engage the pen housing 101, a display 240 and user input means in the form of one or more buttons 250. In the shown embodiment a further activity switch 235 adapted to engage the dose setting member 180 is provided. Alternatively or in addition an acoustic sensor may be provided to detect specific sounds generated by the expelling mechanism during dose setting and dose expelling. The electronic circuitry 210 will typically comprise controller means, e.g. in the form of a generic microprocessor or an ASIC, ROM and RAM memory providing storage for imbedded program code and data, a display controller and a wireless transmitter/receiver.

The add-on device further comprises mounting means (not shown) adapted to releasably mount and securely hold and position the add-on device on the pen housing. For the shown embodiment the add-on device covers the display window for which reason the current dose size shown in the display window has to be captured and displayed on the electronic display 240. Alternatively, the add-on device may be designed to allow the user to view the display window.

The coupling means may be in the form of e.g. a bore allowing the add-on device to slide in place on the pen body, flexible gripping structures allowing the add-on device to be mounted in a perpendicular direction, locking means that will snap in place when the add-on device is mounted on the pen body, or locking means which has to be operated by the user, e.g. a hinged latch member or a sliding member.

As scale drum position and thus dose size determination is based on image capturing and subsequent processing of the captured image data, it is important that the add-on device is correctly positioned in its intended operational position on the drug delivery device. Thus, in order to securely hold and position the add-on device on the pen housing the add-on device may be provided with positioning means adapted to engage a corresponding positioning structure on the pen body. The positioning structure may be in the form of an existing structure provided for a different purpose, e.g. the window opening, or a specific mounting structure, e.g. one or more indents provided on the pen body. In addition to the above-described coupling and positioning means designed to provide a user-recognisable engagement, e.g. by an ensuring "click", the add-on device 200 is provided with a mounting switch 230, e.g. a mechanical micro switch, which is actuated from an off-state to an on-state when the add-on device is mounted on the pen housing.

Figure 5:
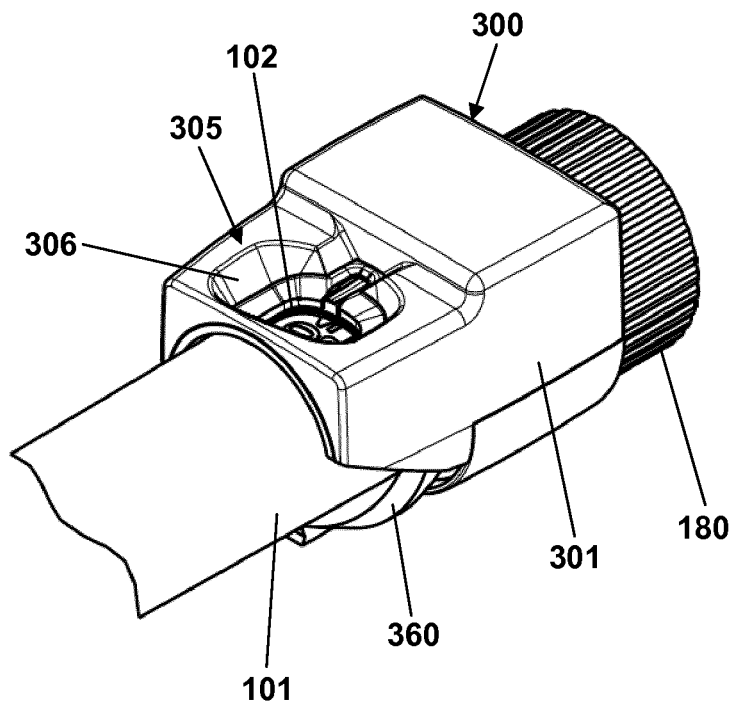
FIG. 5 shows an add-on device mounted on the housing of a drug delivery device.

FIG. 5 shows an add-on device 300 in a state where it has been mounted on the housing 101 of a drug delivery device of the above-described pen type. In contrast to the embodiment of FIG. 4 no user input button is provided. The device as shown is intended primarily to illustrate how an add-on device can be positioned on a pen device allowing a camera device (not shown) to capture images of the scale drum as presented in the housing display window 102. Correspondingly, portions of the add-on device have been removed.

The add-on device 300 as shown comprises a housing 301 with a cavity 305 having a lower opening adapted to be positioned over and in alignment with the housing display window 102. The opening is surrounded by a positioning structure in the form of a downwardly pro-truding lip portion 306 adapted to precisely engage and grip the chamfered edge portion 109 of the display opening, this ensuring that the add-on device can be correctly positioned on the pen housing. As will be explained in greater detail below the lip portion does not fully cover the edge portion surrounding the window opening. The add-on device further comprises a user-operatable locking member 360. The locking member may be designed to prevent locking until the add-on device is correctly positioned on the pen housing with the lip portion seated in the housing display opening. The mounting switch may be arranged to be actuated when the locking member is actuated to its fully closed position.

The above-described add-on device 200 is adapted to be mounted on a pen-formed drug delivery device of the type described above with reference to FIGS. 1-3, such a device comprising a scale drum with a plurality of dose size line markers as well as a window 102 with a pointer 109P. For a given set dose size the pointer will ideally be aligned with a line marker corresponding to that set dose size.

However, due to tolerances the scale drum may not be perfectly aligned rotationally with the pointer, which for a given set dose may result in the pointer not being perfectly aligned with the line marker for the actually set dose. For example, for a "true" set dose of 15 IU the scale drum may be positioned with the pointer arranged between 15 and 16 IU, i.e. at 15½ IU. Correspondingly, when the pointer points at ½ IU this may in fact represent 0 or 1 IU. Indeed, for small doses the relative inaccuracy may be quite significant.

For a typical drug delivery device each line marker on the scale drum is arranged with a rotational distance of 15 degrees, however, due the specific design of the expelling mechanism the distance between the "0" line marking and the "1" line marking may be smaller. For example, in the FlexTouch® pen device the distance between the arrow-formed "0" marking and the "1" line marking corresponds to a rotational distance of 9 degrees. For such a device the tolerances will most likely result in incorrect determination of the positions "0" and "1" due to the shorter distance between the two line markers, i.e. the pointer will point at the "½" position.

The present invention addresses the issue of finding the correct "0" (zero) position by providing zero markings on the drug delivery device which can be captured by the add-on device and which positively indicate whether or not the scale drum is positioned in a given rotational position, e.g. the true zero position in which the scale drum is rotated to its initial stop position irrespective of how the "0" arrow marking is aligned with the pointer.

In summary, the above is achieved by providing corresponding aligning zero markings on the pen housing and the scale drum after the pen device has been assembled. More specifically, a method of manufacturing a drug delivery device is provided, the drug delivery device comprising a drug reservoir or a compartment for receiving a drug reservoir, drug expelling means comprising a rotatable dose setting member allowing a user to set a dose amount of drug to be expelled, a scale drum adapted to rotate relative to the housing during dose setting respectively dose expelling corresponding to an axis of rotation, the amount of rotation corresponding to a set dose respectively the amount of drug remaining to be expelled from a reservoir by the expelling means, the indicator member having an initial rotational position corresponding to no dose amount being set. The device further comprises a housing comprising an opening allowing a user to observe a portion of the scale drum, the opening being surrounded by an edge portion formed by the housing. A pattern is arranged helically on the indicator member and comprises a plurality of indicia, the currently observable indicia indicating to a user the size of a currently set dose amount of drug to be expelled. Next the scale drum is arranged in the initial rotational position (or it is assured that the scale drum is arranged in the initial rotational position), after which a pair of first and second reference zero markers having a predetermined rotational offset is provided on the housing and on the scale drum respectively, e.g. by means of laser engraving. The rotational offset may be zero corresponding to the zero markings being axially aligned.

In alternative embodiments the housing or the scale drum may be provided with a first reference zero marking on one of the components prior to assembly, the second corresponding reference zero marking on the other component being provided after assembly and with the scale drum in the initial position, e.g. the true zero position. Indeed, for such a set-up the latter created zero marking would have to be carefully aligned with the pre-manufactured zero marking. In case the pre-manufactured zero marking is created on the housing then a number of features on the pen housing, e.g. mechanical features, could be used to properly ori-entate the pen relatively to the marking means. In contrast, in case the pre-manufactured zero marking is created on the scale drum, e.g. in the form of the above-described arrow-formed "0" marking or in the form of an additional marking, it would be necessary to identify the rotational position of such a scale drum zero marker in order to properly create an aligned zero marking on the housing.

Figure 6:
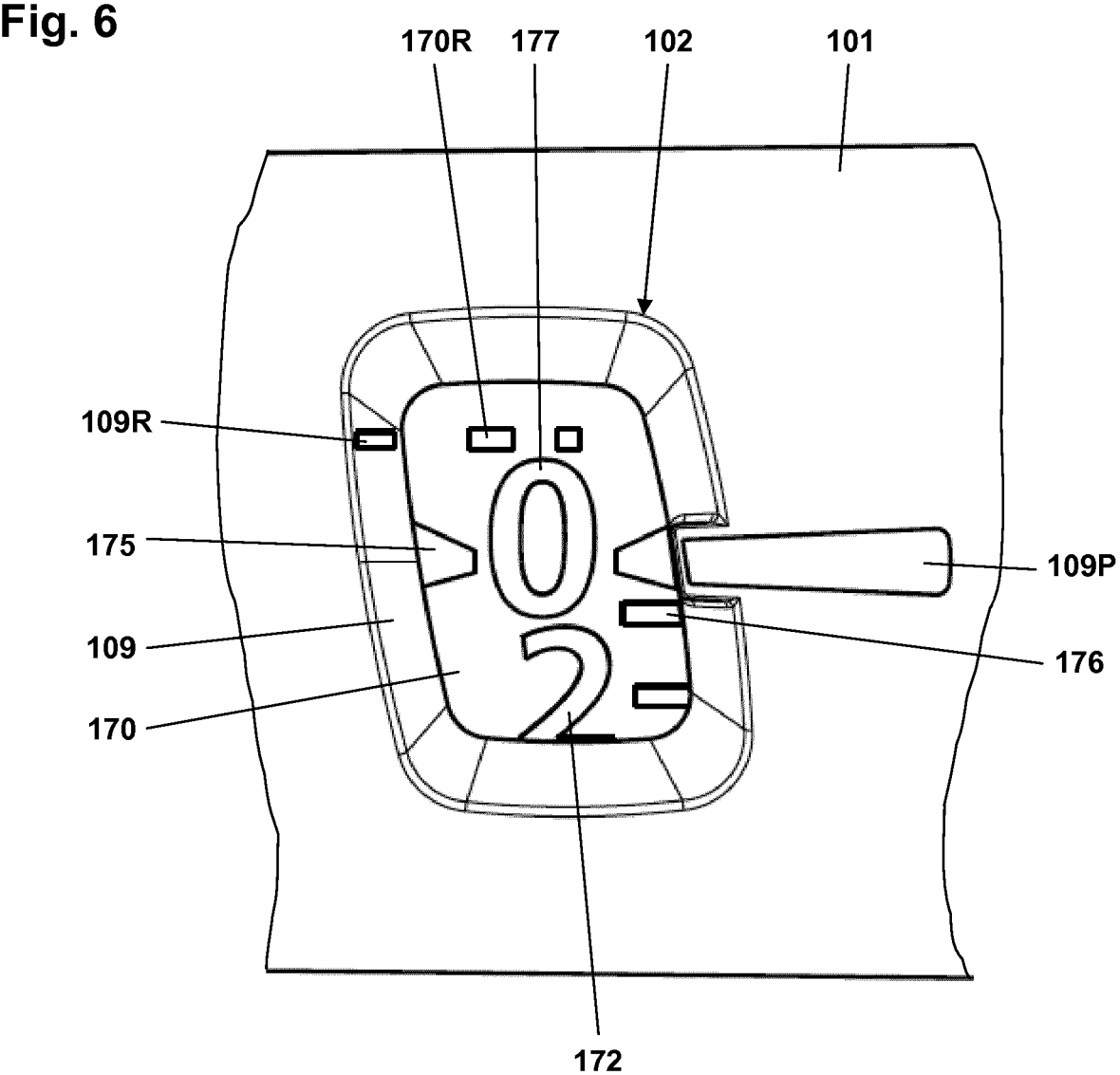
FIG. 6 shows a window portion of a drug delivery device comprising a pair of markings.

FIG. 6 shows a window portion of the drug delivery device described above with reference to FIGS. 1-3, the device comprising a drug expelling mechanism allowing a user to set a dose amount of drug to be expelled in increments of 1 IU. The drug delivery device comprises a scale drum indicator member 170 adapted to rotate relative to the housing 101 during dose setting and dose expelling corresponding to an axis of rotation, the amount of rotation corresponding to a set dose respectively the amount of drug remaining to be expelled from a reservoir by the expelling means, the indicator member having an initial rotational position corresponding to no dose amount being set. The housing 101 comprises an opening or display window 102 allowing a user to observe a portion of the scale drum indicator member 170, the opening being surrounded by a chamfered edge portion 109 and a dose pointer 109P. A pattern comprising a plurality of indicia is arranged helically on the indicator member. In the shown embodiment the indicia comprise a plurality of dose markers 176 as well as a plurality of associated numerals 172 comprising the equal numbers ranging from 0 to 80. The viewable dose marker positioned corresponding to the dose pointer 109P indicates to a user the currently set dose amount of drug to be expelled. The dose marker for 0 UI is in the form of a pair of opposed arrow markers 175 whereas the remaining dose markers are in the form of a single line marker.

The scale drum is provided with an "initial pattern portion" observable by the user as well as by the camera of a mounted add-on device when the scale drum indicator member is positioned in the initial rotational position. In the shown embodiment the scale drum is provided with a "0" indicia 177, a 0 IU arrow marker 175, and a 1 IU line marker 176. In the shown embodiment the "initial pattern portion" is represented by the "upper half" portion of the viewable scale drum comprising at least in part both the "0" indicia 177 and the arrow marker 175. Corresponding to the above-described concept the housing and the scale drum comprises a pair of reference zero markers arranged on the housing respectively the scale drum. In the shown embodiment a housing reference zero marker in the form of a short line marker 109R is arranged on the chamfered edge portion 109, and a scale drum reference zero marker in the form of a dotted line marker 170R is arranged on the scale drum. The two reference zero markers have in the shown initial position a rotational offset of zero degrees, i.e. they are substantially aligned when observed by the user or a mounted camera. As also described above, both the housing reference zero marker 109R and the scale drum reference zero marker 170R may have been provided by e.g. laser engraving after assembly of the device. Alternatively, the housing reference zero marker may be formed integrally with the housing with only the scale drum reference zero marker being provided after assembly of the device, or the scale drum reference zero marker may be formed on the scale drum prior to assembly as part of the scale drum pattern with the housing reference zero marker being provided after assembly of the device.

The shown "dots" of the scale drum reference zero marker 170R may be used to represent a code indicating e.g. the type of drug contained in the drug delivery device. Alternatively the scale drum reference zero marker may be in the form of an unbroken line.

Addressing the issue of correctly determining the "true" initial position of a scale drum an exemplary add-on device, e.g. corresponding to the schematic representation in FIG. 2, is provided with a memory in which data representing the initial pattern portion is stored, e.g. the "0" indicia 177 and/or the arrow marker 175. The capturing means is adapted to capture an image of the "upper" portion of the viewable scale drum, i.e. the portion comprising the initial pattern portion when the scale drum is positioned in its initial position, as well as the portion of the housing comprising the housing reference marker 109R. The processor is adapted to perform a "true zero" determination comprising the steps of (i) capture an image, (ii) perform an image analysis to determine if the captured image comprises the initial pattern portion, (iii) if the captured image comprises the initial pattern portion (indicating that the scale drum may be in the initial position), then (iv) perform an image analysis to determine if the captured image comprises the scale drum reference zero marker, and (v) if the captured image comprises the scale drum reference zero marker, then determine the rotational offset between scale drum reference zero marker and the housing reference zero marker. If the rotational offset between the scale drum reference marker and the housing reference marker corresponds to the pre-set value, e.g. zero degrees, then the scale drum can be determined to be in its initial zero position, this as shown in FIG. 6.

Figure 7A:
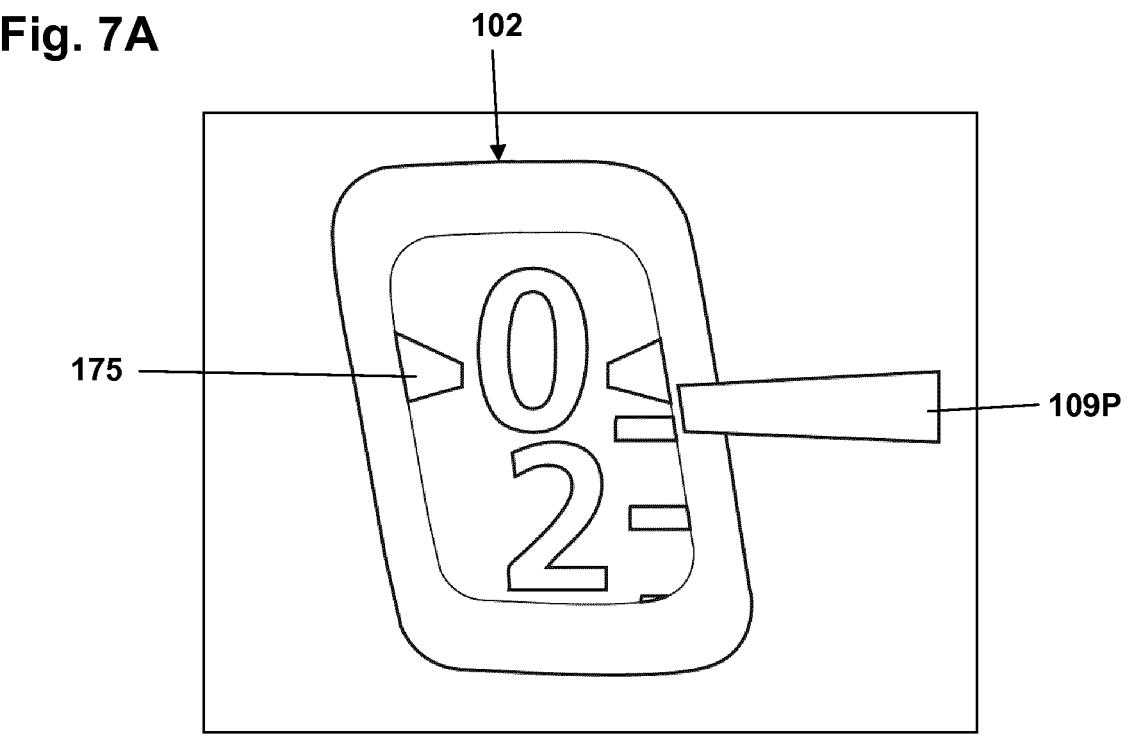
FIGS. 7A and 7B show scale drums in different initial positions.

In FIG. 7A an example for a drug delivery device is shown in which the manufacturing tolerances have resulted in a device in which the dose pointer 109P with the scale drum in its true initial position is arranged corresponding to the "½" position. Correspondingly, in FIG. 7B an example for a drug delivery device is shown in which the manufacturing tolerances have resulted in a device in which the dose pointer 109P with the scale drum in its true initial position is arranged corresponding to the "−½" position. As appears, the situation shown in FIG. 7A also corresponds to a situation in which the scale drum of the drug delivery device of FIG. 7B has been arranged in a true "1" position.

Addressing the above issue, an example in which a drug delivery device comprises a scale drum which due to tolerances is rotationally offset in its initial position will be described, the device being provided with a pair of reference zero markers arranged on the housing respectively the scale drum.

Figure 8A:
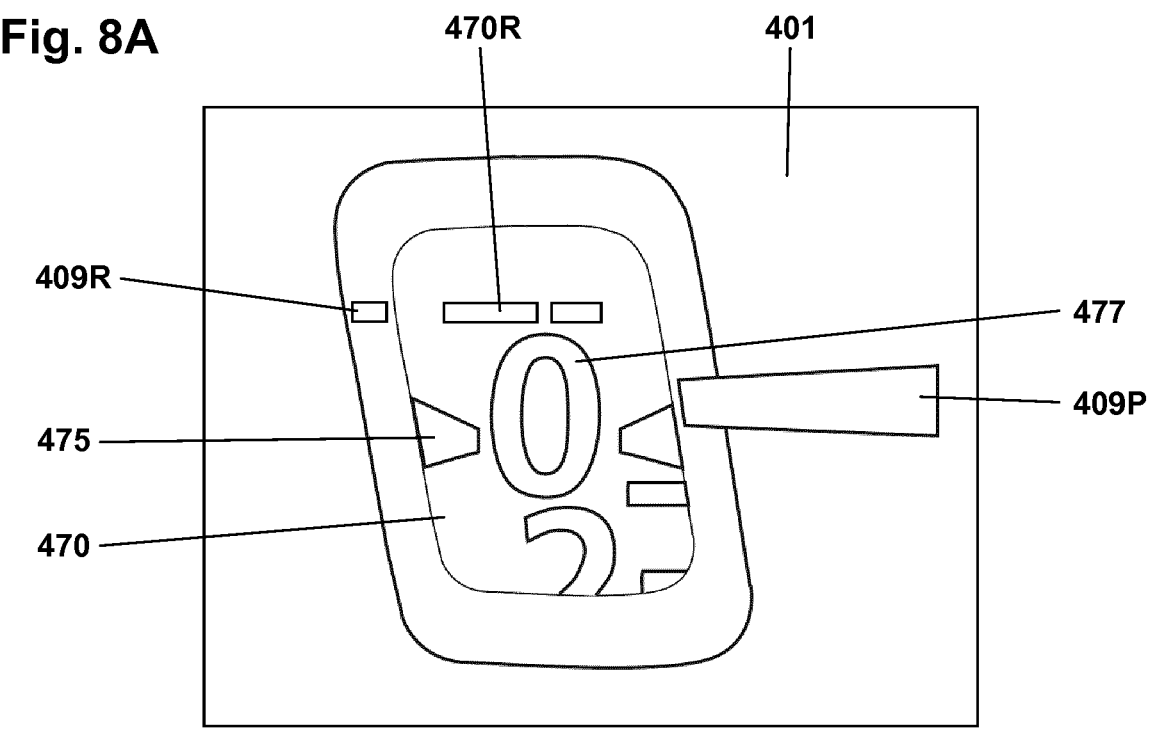
FIGS. 8A and 8B show a window portion of a drug delivery device comprising a pair of markings, the scale drums being positioned in different positions.

More specifically, FIG. 8A shows the window portion of a drug delivery device in which the housing 401 has been provided with a first reference zero marker in the form of housing reference zero marker 409R and in which the scale drum 470 has been provided with a second reference zero marker in the form of scale drum reference zero marker 470R, the pair of reference zero markers having no rotational offset to each other with the scale drum arranged in its shown true initial rotational position. As can be seen, due to tolerances the dose pointer 409P is arranged corresponding to the "−½" position. Correspondingly, when a dose of 1 unit is set as shown in FIG. 8B the dose pointer 409P is arranged corresponding to the "½" position and the scale drum reference zero marker has been rotated out of alignment with the housing reference zero marker.

With a corresponding add-on device mounted, e.g. of the above-described type, the pair of reference zero markers may be used in the following way to determine a true initial scale drum position. When an image is captured the processor will perform an image analysis to determine if the captured image comprises the initial pattern portion. In the shown example the initial pattern portion is represented by the "upper" portions of the "0" indicia 477 and the arrow marker 475, both of which are unique and thus indicate that the scale drum may be positioned in the initial zero position (as the "0" used for the initial zero position is wider than the indicia "0" used in e.g. "10" or "20" it represents a unique marker). Thus, if the captured image comprises the initial pattern portion then a further image analysis is performed to determine if the captured image comprises the scale drum reference zero marker in the form of the dotted line marker 470R. If this is the case a further image analysis is performed to determine the rotational offset between scale drum reference zero marker 470R and the housing reference zero marker 409R. If the rotational offset between the scale drum reference zero marker and the housing reference zero marker corresponds to the pre-set value (here: zero degrees) then the scale drum can be determined to be in its initial zero position, this as shown in FIG. 8A.

Figure 8B:
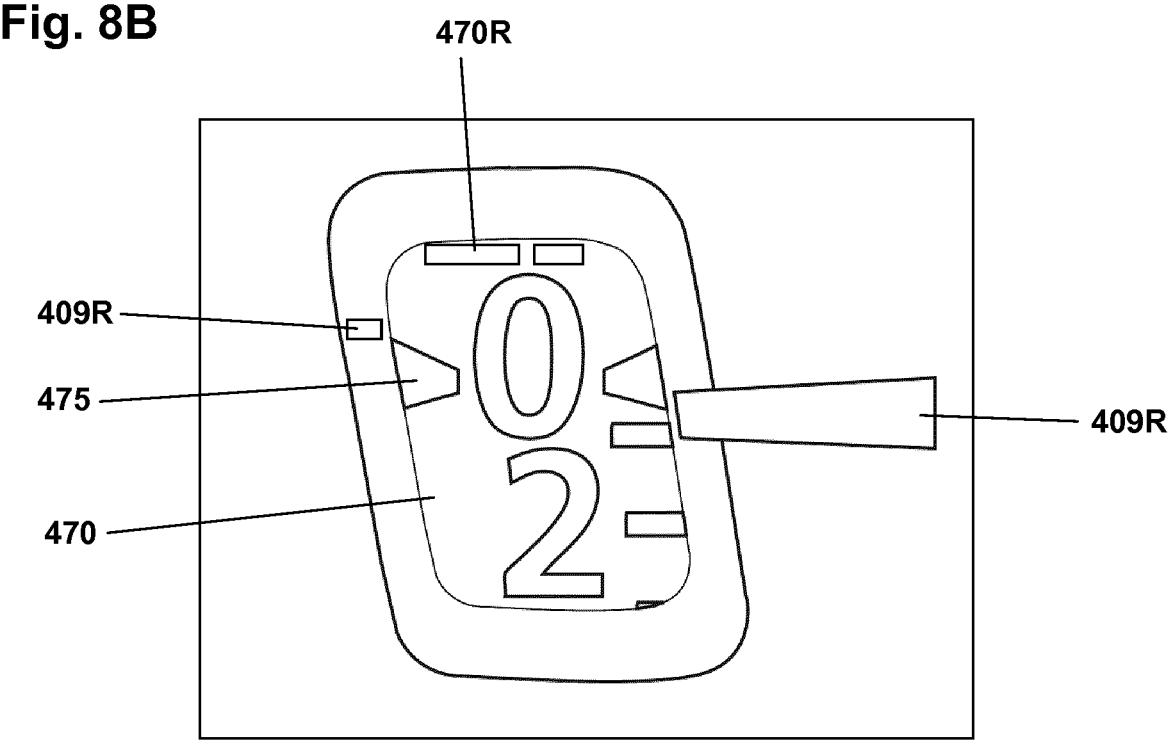

When the scale drum is positioned corresponding to a set or remaining dose of 1 IU as seen in FIG. 8B, the add-on device processor will perform the same analysis, however, as the captured image does not contain the scale drum reference zero marker or the scale drum reference zero marker is not aligned with the housing reference zero marker (as shown in FIG. 8B), no initial scale drum position will be determined.

When a true initial scale drum position has been determined, further analysis of the corresponding captured image may be performed to determine an offset value for the actual device. As will be described below, calculating the actual offset value for a given device may be used to more effectively determine the rotational position of the scale drum for any given rotational position.

Figure 7B:
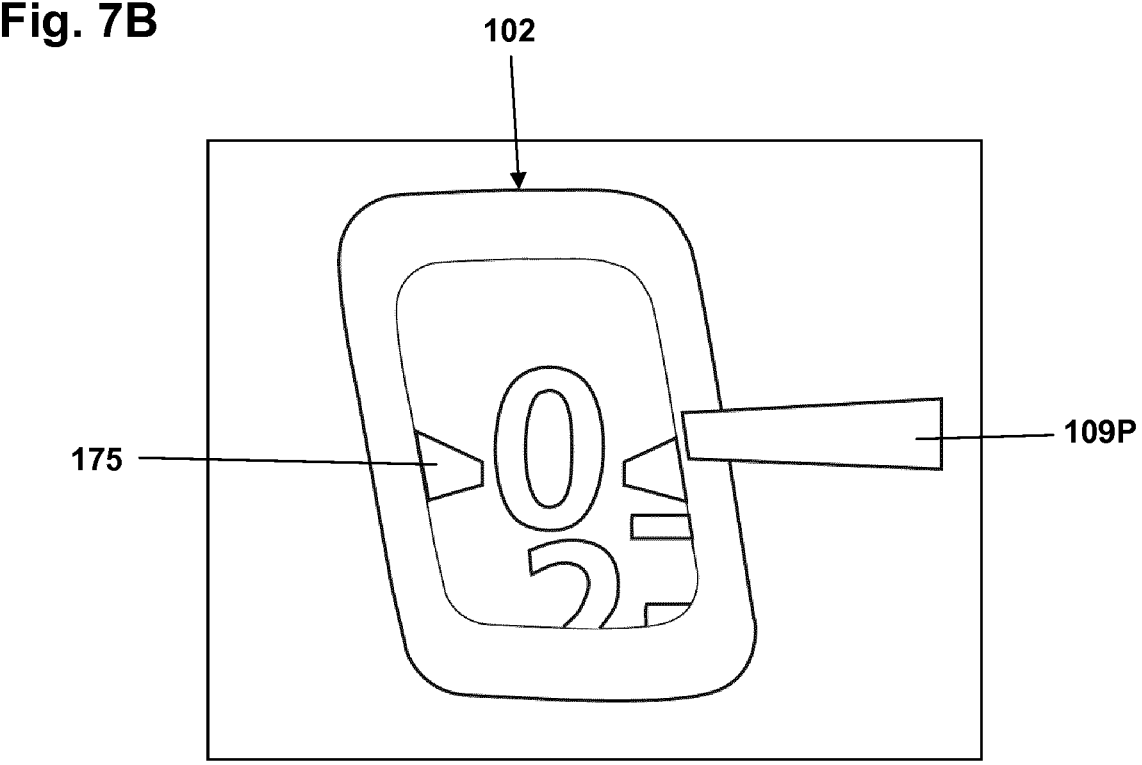
Figure 9A:
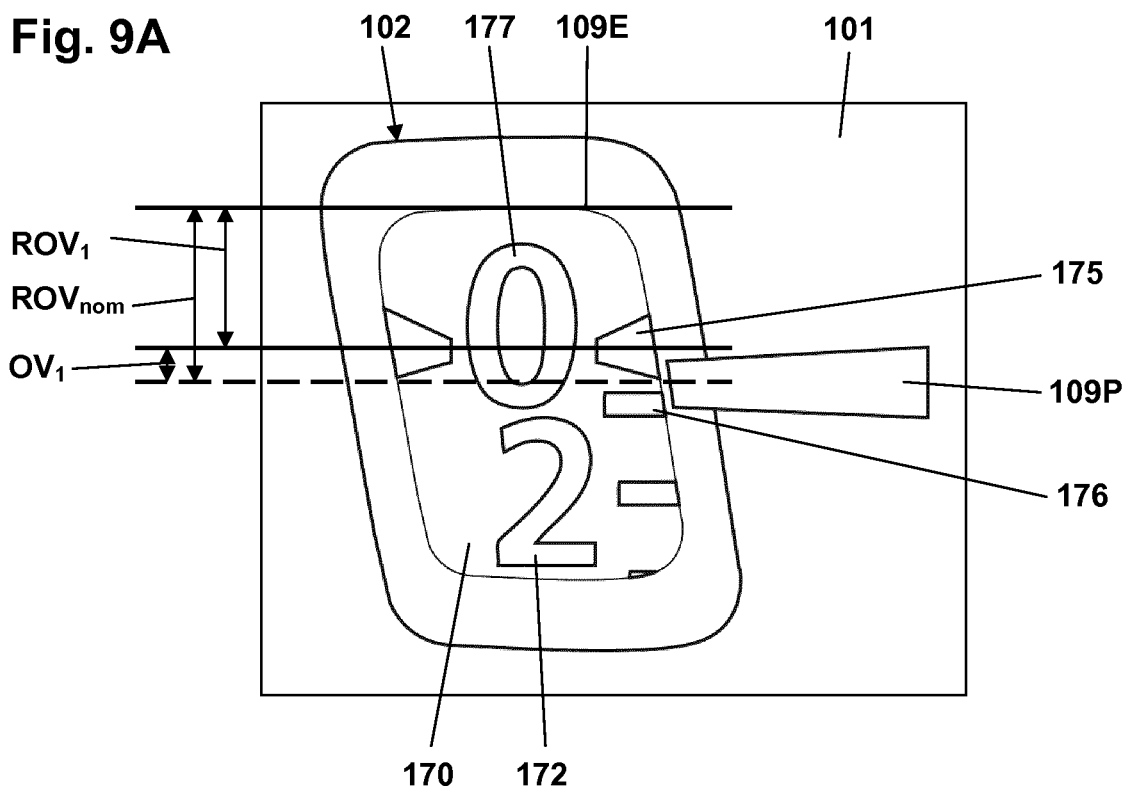
FIGS. 9A and 9B show scale drums in different initial positions illustrating the calculation of offset values.
Figure 9B:
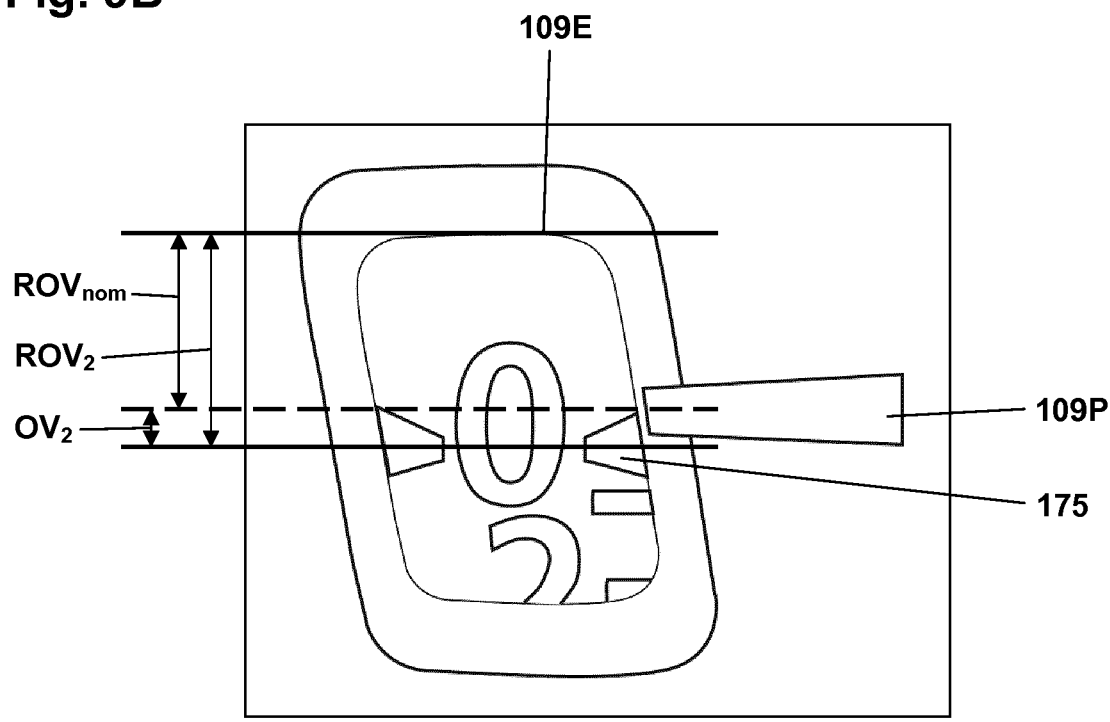

With reference to FIGS. 9A and 9B examples of the determination of an offset value (OV) will be given, the offset value being determined as the difference between an actually determined "reference offset value" (ROV) and a nominal reference offset value (ROV$_{nom}$) The figures correspond to FIGS. 7A and 7B without the pair of reference zero markers being shown. The reference offset value is based on the distance between a housing reference marker and a pattern reference marker. In FIGS. 9A and 9B the housing reference marker is in the form of the "upper" window edge 109E and the pattern reference marker is in the form of the centre line of the arrow markers 175. Alternatively other reference marker may be used. In both figures it has been determined that the scale drum is arranged in the initial zero position.

A determined reference offset value may also be utilized to more safely and efficiently determine the rotational position of the scale drum indicator member, e.g. when the add-on device determines scale drum position by template-matching with a stored representation of the entire scale drum surface image.

Figure 10:
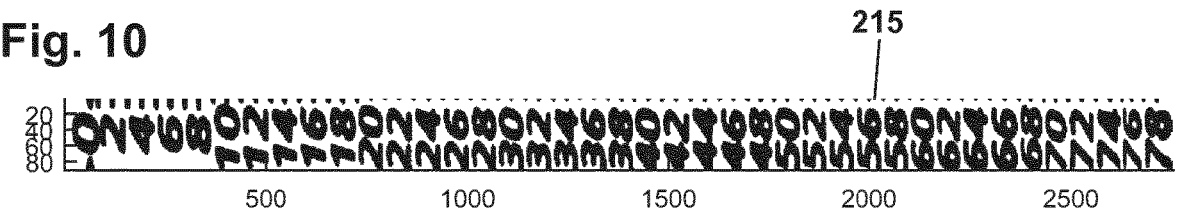
FIG. 10 shows a scale drum reference representation.
Figure 11:
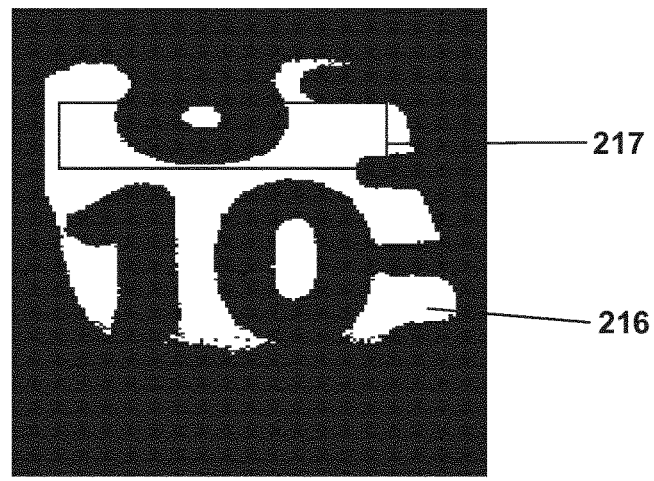
FIG. 11 shows an image capture from a scale drum.
Figure 12:
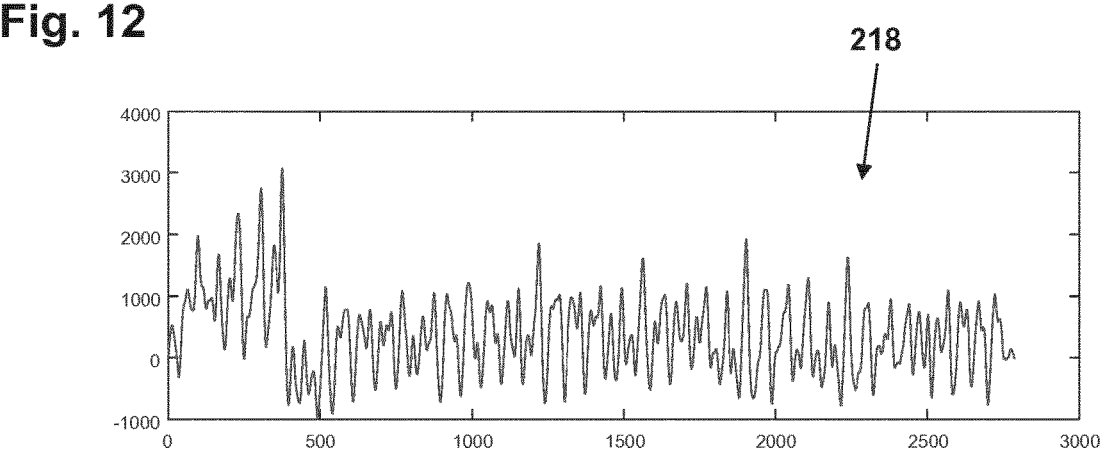
FIG. 12 shows cross correlation of the FIG. 8 image portion to the reference representation.
Figure 13:
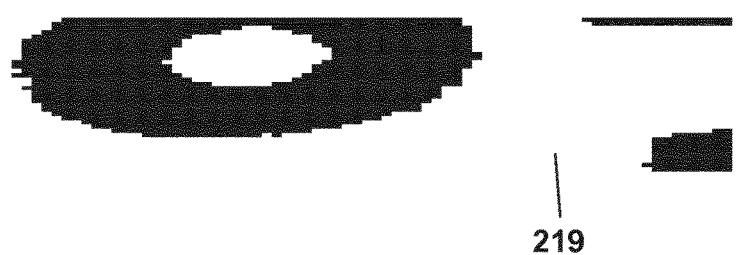
FIG. 13 shows a matched portion of the reference representation.

Correspondingly, FIG. 10 illustrates a template image 215 of the whole scale-drum. The image has been obtained by concatenating parts of successive images from a film where the scale-drum moves from position 80 to position 0. More specifically, the template has been made by concatenating the vertical centre of each frame in the movie, automatically creating a sheared image, this resulting in all digits being tilted as can be seen when compared to the scale drum digits shown in FIG. 11. Alternatively, the ribbon image could be obtained from a CAD-drawing of the scale drum print for a FlexTouch® device, the drawing being cut and sheared to produce a long ribbon. The template image is used as a reference when to determine the position of a specific image. The pixel position (horizontal axis in the above figure) corresponds to the drum position (in degrees, IU or other units). As an example, FIG. 11 shows an image 216 of the scale-drum window where the position corresponds to 10 IU, the rectangle 217 illustrating the area that is used for position detection. FIG. 12 then shows the cross correlation of the rectangle image portion to the reference 215 as a function 218 of pixel position. Searching for the peak reveals a best match at pixel position 341, corresponding to the cut 219 from the reference image as shown in FIG. 13. The reference image at this pixel offset was taken when the scale drum was in a position 9.8 IU. Indeed, if the template image has been created by sheering the digits this also means that the image taken with the camera should be sheered correspondingly before matching with the template.

In general, the captured image should be processed to correspond to the stored template, or, alternatively, the template image should be processed to correspond to the captured images before being stored. More specifically, in addition to the above-described shearing issue, the captured images may be distorted due to e.g. the angular orientation between the camera and the scale drum and the influence of any optical elements arranged in front of the camera. Correspondingly, the template image may be processed before storage to create a "distorted" image which matches the images as actually captured.

As appears, in case the scale drum indicator member is rotationally offset due to tolerances, a captured image for a given rotational position would not correctly correspond to the nominal template image for that rotational position. Correspondingly, if the scale drum rotational offset for a given drug delivery device could be determined, it would be possible to "shift" the template image to match the offset.

In the nominal initial rotational position the arrow marker 175 in FIG. 9A would be arranged exactly corresponding to the centre of the dose pointer 109P and thus have a nominal reference offset value ROV$_{nom}$. If for a given drug delivery device a reference offset value ROV$_1$ has been determined the ROV$_{nom}$ could be used to calculate an actual offset value OV$_1$ as indicated in FIG. 9A, this value corresponding to the offset between an actual captured image portion and its corresponding nominal template image portion. In FIG. 9B a reference offset value ROV$_2$ has been determined and a corresponding offset value OV$_2$ has calculated.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A method of manufacturing and calibrating a drug delivery device, comprising:
   providing the drug delivery device comprising:
      a drug reservoir or a compartment for holding a drug reservoir,
      drug expelling structure comprising a dose setting member allowing a user to set a dose amount of drug to be expelled,
      an indicator member adapted to rotate relative to a housing during dose setting and dose expelling corresponding to an axis of rotation, an amount of rotation corresponding to a set dose, and the amount of drug remaining to be expelled from the drug reservoir by the expelling structure, respectively, the indicator member having an initial rotational position corresponding to no dose amount being set,
      the housing comprising a window allowing the user to observe a portion of the indicator member, the window being surrounded by an edge portion formed by the housing,
      a pattern arranged circumferentially or helically on the indicator member and comprising a plurality of indicia, the currently observable indicia indicating to the user the size of a currently set dose amount of drug to be expelled,
      a housing zero marker on the housing,
   (ii) after step (i), arranging the indicator member in the initial rotational position, and
   (iii) after step (ii), creating an indicator zero marker on the indicator member, the indicator zero marker having a predetermined rotational offset from the housing zero marker.

2. The method as in claim 1, wherein the rotational offset is zero.

3. The method as in claim 1, wherein the housing zero marker and the indicator member zero marker are arranged in the vicinity of each other.

4. The method as in claim 1, wherein the window is an opening.

5. The method as in claim 4, wherein the edge portion is chamfered, the housing zero marker being provided on the chamfer.

6. The method as in claim 1, wherein the window comprises a transparent member arranged in an opening in the housing.

7. The method as in claim 6, wherein the transparent member is mounted in the opening after step (iii).

8. A method of manufacturing a drug delivery system comprising:

manufacturing and calibrating a first drug delivery device according to claim 1, the drug delivery reservoir being provided as a first drug delivery reservoir having a first type of drug formulation and the indicator zero marker comprising a first indicator zero marker comprising a first code indicative of the first type of drug formulation;

manufacturing and calibrating a second drug delivery device according to claim 1, the drug delivery reservoir being provided as a second drug delivery reservoir having a second type of drug formulation and the indicator zero marker comprising a second indicator zero marker comprise a second code indicative of the second type of drug formulation.

9. The method as in claim 8, wherein at least one of the code indicative of the first type of drug formulation and the code indicative of the second type of drug formulation is formed in step (iii).

10. The method as in claim 8, wherein at least one of the code indicative of the first type of drug formulation and the code indicative of the second type of drug formulation is a visual code.

11. The method as in claim 8, wherein at least one of the code indicative of the first type of drug formulation and the code indicative of the second type of drug formulation is visible to a human eye.

12. A method of manufacturing and calibrating a drug delivery device, comprising:

providing the drug delivery device comprising:
 a drug reservoir or a compartment for holding a drug reservoir,
 drug expelling structure comprising a dose setting member allowing a user to set a dose amount of drug to be expelled,
 an indicator member adapted to rotate relative to a housing during dose setting and dose expelling corresponding to an axis of rotation, an amount of rotation corresponding to a set dose, and the amount of drug remaining to be expelled from the drug reservoir by the expelling structure, respectively, the indicator member having an initial rotational position corresponding to no dose amount being set,
 the housing comprising a window allowing the user to observe a portion of the indicator member, the window being surrounded by an edge portion formed by the housing,
 a pattern arranged circumferentially or helically on the indicator member and comprising a plurality of indicia, the currently observable indicia indicating to the user the size of a currently set dose amount of drug to be expelled,
 an indicator zero marker on the indicator member,
(ii) after step (i), arranging the indicator member in the initial rotational position, and
(iii) after step (ii), creating a housing zero marker on the housing, the housing zero marker having a predetermined rotational offset from the indicator zero marker.

13. The method as in claim 12, wherein the rotational offset is zero.

14. The method as in claim 12, wherein the housing zero marker and the indicator zero marker on the indicator member are arranged in the vicinity of each other.

15. The method as in claim 12, wherein the window is an opening.

16. The method as in claim 15, wherein the edge portion is chamfered, the housing zero marker being provided on the chamfer.

17. The method as in claim 12, wherein the window comprises a transparent member arranged in an opening in the housing.

18. The method as in claim 17, wherein the transparent member is mounted in the opening after step (iii).

19. A method of manufacturing a drug delivery system comprising:

manufacturing and calibrating a first drug delivery device according to claim 12, the drug delivery reservoir being provided as a first drug delivery reservoir having a first type of drug formulation and the indicator zero marker comprising a first indicator zero marker comprising a first code indicative of the first type of drug formulation;

manufacturing and calibrating a second drug delivery device according to claim 2, the drug delivery reservoir being provided as a second drug delivery reservoir having a second type of drug formulation and the indicator zero marker comprising a second indicator zero marker comprise a second code indicative of the second type of drug formulation.

20. The method as in claim 19, wherein at least one of the code indicative of the first type of drug formulation and the code indicative of the second type of drug formulation is formed in step (iii).

21. The method as in claim 19, wherein at least one of the code indicative of the first type of drug formulation and the code indicative of the second type of drug formulation is a visual code.

22. The method as in claim 19, wherein at least one of the code indicative of the first type of drug formulation and the code indicative of the second type of drug formulation is visible to a human eye.

23. A method of manufacturing and calibrating a drug delivery device, comprising:

providing the drug delivery device comprising:
 a drug reservoir or a compartment for holding a drug reservoir,
 drug expelling structure comprising a dose setting member allowing a user to set a dose amount of drug to be expelled,
 an indicator member adapted to rotate relative to a housing during dose setting and dose expelling corresponding to an axis of rotation, an amount of rotation corresponding to a set dose, and the amount of drug remaining to be expelled from the drug reservoir by the expelling structure, respectively, the indicator member having an initial rotational position corresponding to no dose amount being set,
 the housing comprising a window allowing the user to observe a portion of the indicator member, the window being surrounded by an edge portion formed by the housing,
 a pattern arranged circumferentially or helically on the indicator member and comprising a plurality of indicia, the currently observable indicia indicating to the user the size of a currently set dose amount of drug to be expelled,
(ii) after step (i), arranging the indicator member in the initial rotational position, and
(iii) after step (ii), creating a housing zero marker on the housing, and an indicator member zero marker on the indicator member, the housing zero marker and the indicator member zero marker having a predetermined rotational offset.

24. The method as in claim 23, wherein the rotational offset is zero.

25. The method as in claim 23, wherein the housing zero marker and the indicator zero marker on the indicator member are arranged in the vicinity of each other.

26. The method as in claim 23, wherein the window is an opening.

27. The method as in claim 26, wherein the edge portion is chamfered, the housing zero marker being provided on the chamfer.

28. The method as in claim 23, wherein the window comprises a transparent member arranged in an opening in the housing.

29. The method as in claim 28, wherein the transparent member is mounted in the opening after step (iii).

30. A method of manufacturing a drug delivery system comprising:
    manufacturing and calibrating a first drug delivery device according to claim 23, the drug delivery reservoir being provided as a first drug delivery reservoir having a first type of drug formulation and the indicator zero marker comprising a first indicator zero marker comprising a first code indicative of the first type of drug formulation;
    manufacturing and calibrating a second drug delivery device according to claim 3, the drug delivery reservoir being provided as a second drug delivery reservoir having a second type of drug formulation and the indicator zero marker comprising a second indicator zero marker comprise a second code indicative of the second type of drug formulation.

31. The method as in claim 30, wherein at least one of the code indicative of the first type of drug formulation and the code indicative of the second type of drug formulation is formed in step (iii).

32. The method as in claim 30, wherein at least one of the code indicative of the first type of drug formulation and the code indicative of the second type of drug formulation is a visual code.

33. The method as in claim 30, wherein at least one of the code indicative of the first type of drug formulation and the code indicative of the second type of drug formulation is visible to a human eye.

\* \* \* \* \*

UNITED STATES PATENT AND TRADEMARK OFFICE
CERTIFICATE OF CORRECTION

PATENT NO. : 11,464,912 B2
APPLICATION NO. : 16/302417
DATED : October 11, 2022
INVENTOR(S) : Bennie Peder Smiszek Pedersen et al.

It is certified that error appears in the above-identified patent and that said Letters Patent is hereby corrected as shown below:

In the Claims

At Column 16, Claim number 1, please replace Line number 25 with the following:
"(i) providing the drug delivery device comprising"

At Column 18, Claim number 19, please replace Line number 21 with the following:
"device according to claim 12, the drug delivery reservoir"

At Column 20, Claim number 30, please replace Line number 6 with the following:
"device according to claim 23, the drug delivery reservoir"

Signed and Sealed this
Eighteenth Day of April, 2023

Katherine Kelly Vidal
*Director of the United States Patent and Trademark Office*